United States Patent
Nakamura et al.

(10) Patent No.: US 9,453,817 B2
(45) Date of Patent: Sep. 27, 2016

(54) NONDESTRUCTIVE INSPECTION DEVICE USING ALTERNATING MAGNETIC FIELD, AND NONDESTRUCTIVE INSPECTION METHOD

(71) Applicant: DAINICHI Machine and Engineering Co., Ltd., Yokohama-shi (JP)

(72) Inventors: Kunihiko Nakamura, Kanagawa (JP); Gijun Idei, Kanagawa (JP)

(73) Assignee: DAINICHI Machine and Engineering Co., Ltd., Yokohama-shi (JP)

( * ) Notice: Subject to any disclaimer, the term of this patent is extended or adjusted under 35 U.S.C. 154(b) by 162 days.

(21) Appl. No.: 13/965,958

(22) Filed: Aug. 13, 2013

(65) Prior Publication Data
US 2014/0055130 A1    Feb. 27, 2014

Related U.S. Application Data

(63) Continuation of application No. PCT/JP2012/052836, filed on Feb. 8, 2012.

(30) Foreign Application Priority Data

Feb. 18, 2011    (JP) .................................. 2011-049580

(51) Int. Cl.
*G01N 27/82*    (2006.01)
*G01N 27/90*    (2006.01)

(52) U.S. Cl.
CPC .............. *G01N 27/90* (2013.01); *G01N 27/82* (2013.01); *G01N 27/9046* (2013.01); *G01N 27/9033* (2013.01)

(58) Field of Classification Search
CPC ..................... G01N 27/9046; G01N 27/9033; G01N 27/82
USPC .............................. 324/240, 238, 239, 262
See application file for complete search history.

(56) References Cited

U.S. PATENT DOCUMENTS 3,823,368 A * 7/1974 Mansson et al. ............. 324/233
3,916,301 A * 10/1975 Vild et al. ..................... 324/226
(Continued)

FOREIGN PATENT DOCUMENTS

EP    0 015 822 A1    9/1980
GB    2 292 222 A     2/1996
(Continued)

OTHER PUBLICATIONS

Extended European Search Report issued Jun. 4, 2014 in Patent Application No. 12746911.2.
(Continued)

*Primary Examiner* — Reena Aurora
(74) *Attorney, Agent, or Firm* — Oblon, McClelland, Maier & Neustadt, L.L.P.

(57) ABSTRACT

In conventional non-destructive inspection devices using magnetism, the subject of inspection was limited to the surface layer of the test object as a result of the skin effect, and it was not possible to perform flaw detection inspection at the interior or reverse surface of thick-structured test objects. The effect of the surface effect was eliminated by imparting an external signal canceling the detection output of the test object surface layer from the detection output of a magnetic field resulting from eddy currents induced in the test object. As a result, it has become possible to extract the detection output of the test object interior that had been masked by the detection output of the test object surface layer, and it has become possible to perform thickness inspection and flaw detection of the reverse surface and interior or a test object.

8 Claims, 12 Drawing Sheets

(56) References Cited

U.S. PATENT DOCUMENTS

| | | | |
|---|---|---|---|
| 4,191,922 A | | 3/1980 | Harris et al. |
| 4,322,683 A | | 3/1982 | Vieira et al. |
| 4,799,010 A | * | 1/1989 | Muller .......................... 324/240 |
| 4,881,031 A | * | 11/1989 | Pfisterer et al. .............. 324/233 |
| 5,391,988 A | | 2/1995 | Kitagawa |
| 5,689,183 A | | 11/1997 | Kohama |
| 2004/0046550 A1 | | 3/2004 | Kondo |
| 2008/0074109 A1 | | 3/2008 | Tsukada et al. |

FOREIGN PATENT DOCUMENTS

| | | | |
|---|---|---|---|
| JP | 56-130652 | | 10/1981 |
| JP | 10293122 | * | 11/1988 |
| JP | 2622536 | | 4/1997 |
| JP | 3266128 | | 1/2002 |
| JP | WO 03/027659 A1 | | 4/2003 |
| JP | 3753499 | | 12/2005 |
| JP | 3896489 | | 1/2007 |
| JP | 2010-048552 | | 3/2010 |
| WO | WO 2004/005912 A2 | | 1/2004 |
| WO | WO 2004/005912 A3 | | 1/2004 |

OTHER PUBLICATIONS

International Search Report issued May 1, 2012 in PCT/JP2012/052836, filed Feb. 8, 2012, 4 pages with English translation.

* cited by examiner

NONDESTRUCTIVE INSPECTION DEVICE USING ALTERNATING MAGNETIC FIELD, AND NONDESTRUCTIVE INSPECTION METHOD

CROSS REFERENCE TO RELATED APPLICATION

This application is a Continuation of PCT App. No. PCT/JP2012/052836, filed on Feb. 8, 2012, and claims priority to Japanese Patent App. No. 2011-049580, filed on Feb. 18, 2011, the contents of both of which are incorporated herein by reference.

TECHNICAL FIELD

The present invention relates to an apparatus and method using electromagnetic induction to inspect a sample for defects by applying an alternating magnetic field to a conductive sample and detecting the magnetic field caused by eddy currents generated in the sample.

BACKGROUND ART

An example of a conventional method of defect inspection by eddy currents using electromagnetic induction is disclosed in JP-B 3753499 (Patent Document 1). Patent Document 1 describes arrangements to detect at least one of an output voltage difference and a phase difference between detection signals induced in two detection coils oriented perpendicularly with respect to an excitation coil, thereby increasing the detected output voltage and enabling the damage conditions such as cracks in the surfaces of steel frames covered with fire resistant coatings inside buildings to be inspected without stripping away the coating material. However, with such an arrangement, a skin effect causes the magnetic field to decrease exponentially in the depth direction of the sample (steel frame), so damage can only be detected at the surface of the sample (steel frame) covered by the coating material, and it is not possible to inspect for damage inside or on the back surface of the sample. This problem is not limited to Patent Document 1, and while many types of eddy current defect inspection apparatus, eddy current defect inspection methods and defect inspection probes (sensors) using electromagnetic induction have been proposed, it is a serious problem that is common to all of them.

Additionally, as another example of a conventional inspection device, JP-B 3266128 (Patent Document 2) discloses an invention for performing defect inspection by detecting leaked magnetic flux. In Patent Document 2, a plurality of magnetic sensors are arranged along the direction of magnetization of a magnetizer, leaked magnetic flux corresponding to the same positions on the sample is detected, and the measurement results for a plurality of magnetic sensors are computed, thereby reducing noise and detecting internal defects inside the sample. However, with such an arrangement, the end surface of a magnetizer is oriented not roughly perpendicular to the sample surface, but along the sample. However, in that case, only a portion of the magnetic field of the magnetizer is applied to the sample, moreover in a diagonal direction with respect to the sample, so the magnetic field of the magnetizer is not effectively applied to the sample. More importantly, the detection sensor is positioned on the back side of the sample, so the detection sensor detects the magnetic field (leaked magnetic flux) that has passed through the sample, but the magnetic field is exponentially reduced in the depth direction of the sample due to the skin effect, as a result of which the leaked magnetic flux is extremely weak. Additionally, a plurality of magnetic sensors must be provided and results measured by changing the magnetization conditions must be computed, making inspection considerably complicated. When performing inspection by detecting leaked magnetic flux in this manner, the leaked magnetic flux becomes extremely weak due to the skin effect for the reasons described above, thus inevitably limiting the inspection. In the examples of Patent Document 2, the objects being inspected are 1 mm-thick steel sheets, and the lift-off (distance between sample and detection sensor) is only 1 mm. Thus, in devices that perform inspection by detecting leaked magnetic flux, the skin effect limits what can be inspected to thin materials, making them entirely inapplicable to defect detection inside or on the back side of thick materials.

Additionally, as another example of a conventional inspection device, a proposal to perform defect inspection using the transmitted magnetic flux transmitted through the interior of a sample is disclosed in JP-A 2010-48552 (Patent Document 3). In Patent Document 3, defects inside a sample are detected by measuring the magnetic potential difference between two points of the transmitted magnetic flux transmitted through the interior of a sample (although Patent Document 3 uses the expression "magnetic potential", there is interlinkage from the coil through which current applied to the magnetic circuit flows, as shown in FIG. 1 and FIG. 3 which is a simplified version thereof, so it cannot be treated like electrical potential, and the concept of magnetic potential as used in Patent Document 3 is physically meaningless). The detection principles are shown in the schematic diagram of FIG. 3 in Patent Document 3, and are explained as follows. In other words, the excitation core, the sample and the pickup core can be considered to constitute a pathway for magnetic flux. The magnetic flux applied from the excitation core to the sample flows through this pathway, and if there is a defect inside the sample, a large magnetic resistance will occur in the sample, so the output of the magnetic potential difference measuring means (detection coil) provided in the pickup core will change. As a result, so it is explained, defects inside the sample can be detected. However, the magnetic field (magnetic flux) applied from the excitation core to the sample will not flow uniformly inside the sample due to the skin effect, being greatest at the surface of application to the sample and exponentially decreasing toward the inside of the sample. As long as a normal alternating magnetic field is used, a transmitted magnetic flux that flows uniformly through the inside of the sample such as shown in FIG. 3 of Patent Document 3 will not exist. The applied magnetic field has its maximum intensity at the surface of the sample. While the frequency of the applied magnetic flux can be lowered by controlling the attenuation of the magnetic flux inside the sample to some degree, it is extremely difficult to pass a uniform transmitted magnetic flux through a sample. Even if it were somehow possible to apply and transmit an ultralow frequency much lower than 1 Hz, the detected output voltage of the coil is proportional to the square of the applied frequency, so the detection efficiency would be drastically reduced. For example, if the detected output at 1 kHz is 1 V, then the output at 0.1 Hz will be 0.01 μV, which would be drowned out by noise and make the detected signal very difficult to handle. Furthermore, the ultralow frequencies require the electronic circuits in the device to be compatible with ultralow frequencies, and make the data capture time longer, making fast measurements impossible, which is impractical. Thus, inspection using transmitted magnetic flux has the problem that the skin effect prevents the transmitted magnetic flux from flowing uniformly inside the samples, making it inapplicable to defect inspection inside or on the back surface of samples.

Additionally, as another example of a conventional inspection device, in JP-B 3896489 (Patent Document 4), foreign articles such as metal conductors contained in the object of measurement are detected by applying an alternating magnetic field to the object of measurement and studying the magnetic response signal of the magnetic sensor. The detection signals of the magnetic sensor are composed of the magnetic field that the applied alternating magnetic field creates at the position of the magnetic sensor and the magnetic field due to eddy currents generated by a metal conductor contained in the object of measurement (having a 90 degree phase lag with respect to the applied alternating magnetic field). When detecting foreign articles such as metal conductors, the magnetic field created by the applied alternating magnetic field at the position of the magnetic sensor becomes noise. By removing this alternating magnetic field with a cancellation coil, the detection sensitivity for the magnetic field due to eddy currents generated in metal conductors can be raised, enabling inspection for the presence or absence of foreign articles such as metal conductors contained in the object of measurement. Accordingly, in Patent Document 4, the magnetic field created by the applied alternating magnetic field at the position of the magnetic sensor is removed by a cancellation coil, thereby raising the detection sensitivity of the magnetic field due to eddy currents generated by metal conductors contained in the object of measurement, so the purpose is to inspect for the presence or absence of foreign articles such as metal conductors, and not to inspect the inside of metal conductors contained in the object of measurement.

RELATED ART DOCUMENTS

Patent Documents

Patent Document 1: JP-B 3753499
Patent Document 2: JP-B 3266128
Patent Document 3: JP-A 2010-48552
Patent Document 4: JP-B 3896489

SUMMARY OF THE INVENTION

Problems to be Solved by the Invention

In non-destructive inspection using magnetic fields as represented by eddy current defect inspection, an alternating magnetic field is applied to a sample. As a result, eddy currents are induced in the sample in accordance with the skin effect, and the magnetic field generated by the eddy currents is detected by a detection coil. Since the skin effect causes the transmission of the applied magnetic field to decrease exponentially in the depth direction of the sample, the output from the magnetic field due to the eddy currents flowing at the surface of the sample is strong, while the output from the magnetic field due to eddy currents inside the sample is very weak. The signals detected by the detection coil (AC signals) are detected with these outputs mixed. In other words, the high output of the surface portion of the sample will be masked by the small output of the interior of the sample. Although the detected output (AC signal) is rectified/detected and converted to a DC voltage in an electronic circuit, the low output of the interior of the sample will be masked and very little reflected in the rectified and detected DC voltage. This is an essential problem that is still not resolved for defect inspection of the interior or back surface of samples such as thick materials, and a solution is sought.

The present invention has been proposed in view of such circumstances in order to solve the above-described problems, and the purpose is to offer art enabling defect inspection of the inside and back surface of a sample. More specifically, the invention enables defect inspection of the inside or back surface of a sample and inspection of thickness changes or the like, by providing an external signal canceling the detected output of the surface portion of the sample to the detected output of a detection coil, and extracting the detected output inside the sample which was masked by the detected output of the surface portion of the sample.

Means for Solving the Problems

In order to achieve the above purpose, a first embodiment of the present invention is a non-destructive inspection device using an alternating magnetic field, comprising a signal waveform generator; an excitation coil capable of applying an alternating magnetic field to a sample; a detection coil positioned near the excitation coil for sensing a magnetic field due to eddy currents generated from the sample; a circuit comprising a circuit for generating a sinusoidal signal of approximately equal amplitude and opposite phase with respect to a detected signal of the detection coil, for outputting a sum of an output of the opposite-phase sinusoidal signal generating circuit and the detected signal of the detection coil; and circuit means for detecting a remainder signal of the sum signal output; wherein a detected output of a surface portion of the sample due to the skin effect is canceled to detect the output inside the sample which was masked by the detected output of the surface portion of the sample.

A second embodiment of the present invention is a non-destructive inspection device using an alternating magnetic field, comprising a signal waveform generator; an excitation coil capable of applying an alternating magnetic field to a sample; a detection coil positioned near the excitation coil for sensing a magnetic field due to eddy currents generated from the sample; a circuit comprising a circuit for generating a sinusoidal signal of approximately equal amplitude and in-phase with respect to a detected signal of the detection coil, for outputting a difference between an output of the in-phase sinusoidal signal generating circuit and the detected signal of the detection coil; and circuit means for detecting a remainder signal of the difference signal output; wherein a detected output of a surface portion of the sample due to the skin effect is canceled to detect the output inside the sample which was masked by the detected output of the surface portion of the sample.

A third embodiment of the present invention is a non-destructive inspection device according to the first or second embodiment, wherein the sample is a material having electrical conductivity.

A fourth embodiment of the present invention is a non-destructive inspection device according to the first or second embodiment, wherein the circuit means for detecting is a synchronous detection circuit.

A fifth embodiment of the present invention is a non-destructive inspection method for a sample, comprising outputting a signal using a signal waveform generator; applying an alternating magnetic field to the sample using an excitation coil; detecting a magnetic field due to eddy currents generated from the sample using a detection coil positioned near the excitation coil; outputting a sum of a detected signal of the detection coil and a sinusoidal signal of approximately equal amplitude and opposite phase with respect to the detected signal of the detection coil; and detecting a remainder signal of the sum signal output; wherein a detected output of a surface portion of the sample due to the skin effect is canceled to detect the output inside the sample which was masked by the detected output of the surface portion of the sample.

A sixth embodiment of the present invention is a non-destructive inspection method for a sample, comprising outputting a signal using a signal waveform generator; applying an alternating magnetic field to the sample using an excitation coil; detecting a magnetic field due to eddy currents generated from the sample using a detection coil positioned near the excitation coil; outputting a difference between a detected signal of the detection coil and a sinusoidal signal of approximately equal amplitude and in-phase with respect to the detected signal of the detection coil; and detecting a remainder signal of the difference signal output; wherein a detected output of a surface portion of the sample due to the skin effect is canceled to detect the output inside the sample which was masked by the detected output of the surface portion of the sample.

Effects of the Invention

According to the present invention, the detected output due to eddy currents at the sample surface portion which is the dominant component of the detected output signal of the detection coil can be cancelled. The detected output (voltage) of the detection coil is observed as the sum of detected voltages due to all eddy currents induced in the sample, but the detected output of the magnetic field due to eddy currents generated at the sample surface is the greatest, and in progressing further inside the sample, the amplitude of the detected output of the magnetic field exponentially decreases relative to the sample surface and a phase lag occurs. This phase lag is proportional to the square root of the product of the excitation angular frequency, conductivity and magnetic permeability of the sample. This sum (addition) of detected outputs at the surface portion of the sample manifests as the dominant component in the detected output of the detection coil. Therefore, the detected output component corresponding to the sample surface portion can be canceled out from the detected output of the detection coil by applying and adding to the detected output of the detection coil an external sinusoidal signal of the same amplitude and opposite phase, or applying and subtracting an external sinusoidal signal of the same amplitude and same phase, thereby simply and effectively extracting the detected output component corresponding to the inside of the sample which was masked by the detected output component corresponding to the surface portion. The sum signal or difference signal indicating the detected component corresponding to the inside of the sample obtained in this way is of a small signal output differing in phase from the detected output of the detection coil, but the high output of the surface portion has been removed, so it can be amplified at a high gain as needed using an amplification circuit, enabling the detected output component corresponding to just the inside of the sample which is to be inspected to be amplified to a sufficiently large signal. Additionally, this sum signal or difference signal is a computed signal obtained by applying and adding or subtracting an external sinusoidal signal of the same amplitude and opposite phase or an external sinusoidal signal of the same amplitude and same phase with respect to the detection coil output, and when there is damage such as a crack in the surface portion at a new inspection position (for example, a portion where the detection coil has been moved on the sample for scanning or the like), route changes in the eddy currents induced in the surface portion can change the detected output at the surface portion, resulting in a difference with the external sinusoidal signal applied at the time of generation of the sum signal or difference signal. Therefore, cracks in the surface portion can also be detected. In other words, by applying and adding or subtracting an external sinusoidal signal of the same amplitude and opposite phase or an external sinusoidal signal of the same amplitude and same phase with respect to the detection coil output, the inside of the sample can be inspected for thickness or damage to the back surface of the sample at a high performance, while at the same time being able to detect damage to the sample surface. Furthermore, the detected output is reduced in accordance with the lift-off (the distance from the detection sensor to the sample), so there has conventionally been a problem of not being able to have a large lift-off, but in the present invention, the large output of the surface portion is removed from the detected output, enabling amplification at a high gain, so the lift-off can be significantly increased. In other words, as explained in detail in the examples described below, damage to the inner wall of an inner pipe of a double pipe, which is not conventionally detectable, was able to be detected from the surface of the outer pipe. Additionally, it has become possible to detect changes in thickness of carbon steel pipes more than 10 mm thick, even with a lift-off and with high precision. Additionally, it has become possible to detect the thickness of a steel pipe or damage to the inner walls of a pipe covered by a metallic outer covering and a condensation-preventing material tens of millimeters thick, with high precision from outside the condensation-preventing material with a cover of covering material. Furthermore, the detection of microscopic flaws formed near welding portions on the inner walls of joint pipes of different materials such as stainless steel and carbon steel have become possible. These represent only a few examples of non-destructive inspection devices according to the present invention, and the non-destructive inspection devices using a magnetic field according to the present invention enable the interior or back surfaces of thick materials including pipes to be inspected for defects with a high lift-off, which has been a matter of concern for years.

MODES FOR CARRYING OUT THE INVENTION

Herebelow, an embodiment of the present invention will be explained with reference to the drawings.

Figure 1:
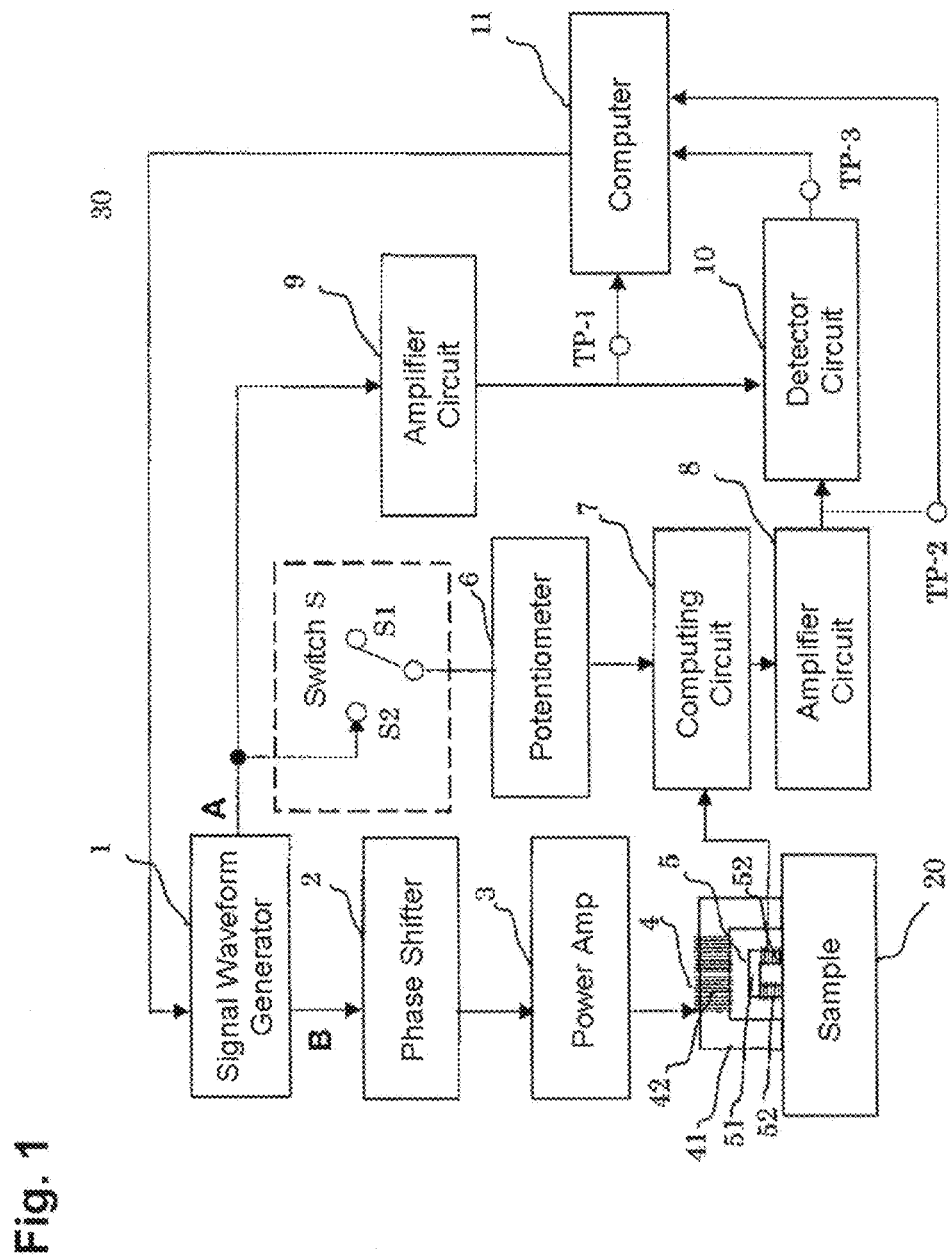
FIG. 1 is a block diagram showing the structure of a non-destructive inspection device according to the present invention.

FIG. 1 is a block diagram showing the structure of a non-destructive inspection device 30 using a magnetic field according to the present invention. As shown in this drawing, the non-destructive inspection device using a magnetic field of the present embodiment comprises a computer 11, a signal waveform generator 1, a phase shifter 2, a power amp 3, an excitation applying means 4, a detecting means 5, a potentiometer 6 and computing circuit 7, an amplifier circuit 8, an amplifier circuit 9 and a detector circuit 10.

The sample 20 is the object of inspection of the non-destructive inspection device 30 using a magnetic field, and may be of any material having conductivity such as carbon steel, stainless steel, aluminum, copper, inconel, zirconium or the like.

The computer 11, in addition to following input instructions from an operator, not shown, to control the voltage, phase and frequency of an AC signal generated by the signal waveform generator 1, also displays a check terminal TP-2 for analyzing the output of the amplifier circuit 8, a check terminal TP-1 for analyzing the output of the amplifier circuit 9, and a check terminal TP-3 for analyzing the output of the detector circuit 10, and performs computations on the output of a detector circuit 10 in accordance with application software, not shown, installed on the computer 11. This detector circuit 10 is preferably a synchronous detector circuit.

The signal waveform generator 1 is capable of simultaneously outputting at least two signal waveforms (FIG. 1 shows two outputs A and B). These at least two signal waveform outputs can be separately set as to the type of waveform, frequency, voltage and phase in accordance with instructions from the computer 11 or a function of the signal waveform generator 1. One of the outputs B is supplied to the power amp 3 and the other output A is supplied as a reference signal through the amplifier circuit 9 and contact point S2 of switch S to the potentiometer 6. The amplifier circuit 8 and amplifier circuit 9 should preferably be a DC-coupled amplifier circuit with constant amplitude and no phase shift across a wide frequency band from DC to the frequency used for measurement. Additionally, while an AC-coupled amplifier circuit with constant amplitude and no phase shift across a wide frequency band from DC to the frequency used for measurement could be used, the use of a DC-coupled amplifier circuit is naturally more desirable when considering the transient response properties when the detection signal is changed by measuring means such as scans mentioned below. Additionally, in order to make phase comparison easier for the amplifier circuit 9, means for waveform rectification or the like of a signal holding only phase information such as a square wave is included at an output stage thereof.

Figure 12:
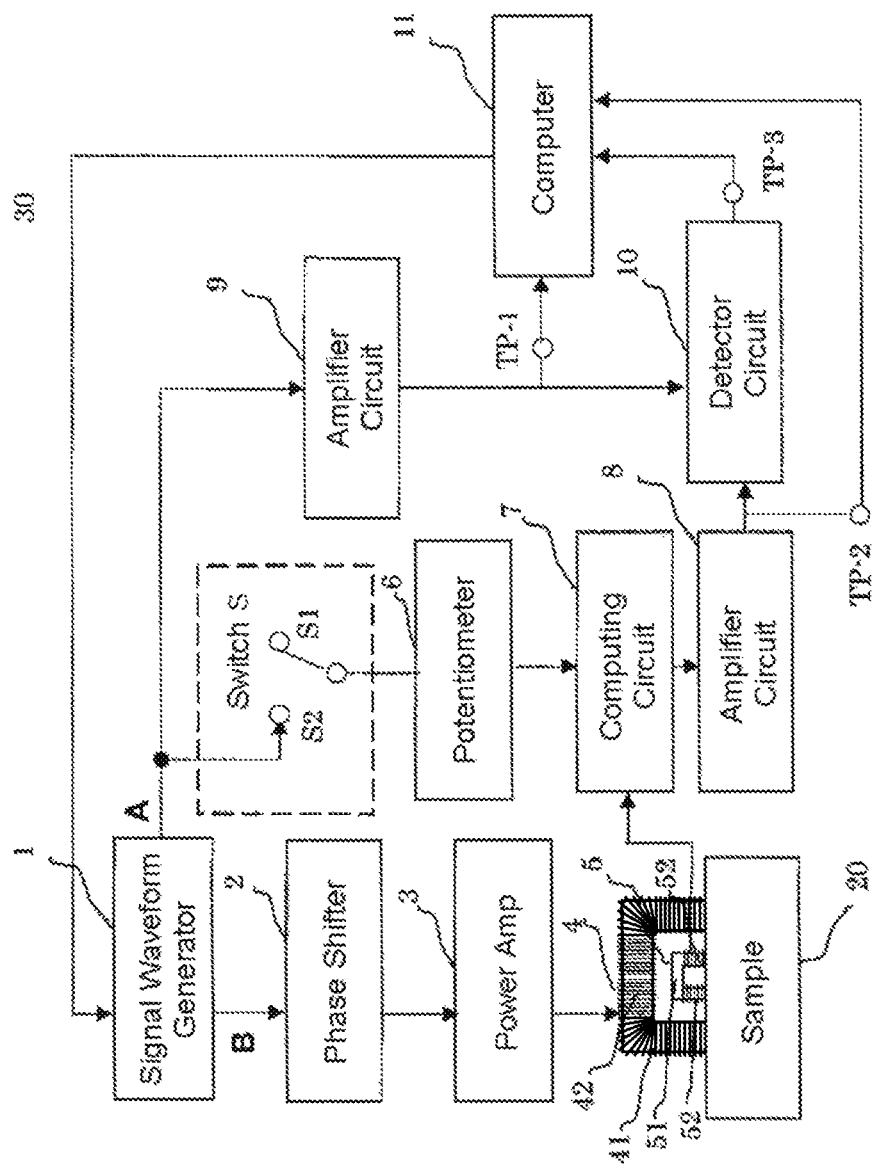
FIG. 12 is a block diagram showing another structure of a non-destructive inspection device according to the present invention.

The excitation means 4 comprises an excitation core 41 and an excitation coil 42, and applies a magnetic field to a sample 20 in accordance with a current supplied from the power amp 3. The excitation core 41 may, for example, be bracket-shaped, with the axial directions of both legs being oriented roughly perpendicular to the sample. The excitation coil 42 is wound along the outer circumference of the excitation core 41. The excitation coil 42 may be wound over the entire circumference of the excitation core 41, or only partially wound. FIG. 1 shows an arrangement in which it is wound only on a portion of the excitation core. FIG. 12 shows a corresponding arrangement in which it is wound over the entire circumference of the excitation core. As another example of partial winding, when wound on both legs of a bracket shape, one leg is wound clockwise and the other leg is wound counterclockwise, and the end of the winding of one lea is coupled to the beginning of the winding of the other leg to form a single continuous coil. In other words, it is arranged so that the magnetic field in the excitation core 41 is oriented in one direction at a certain instant when current is applied to the excitation coil 42.

The detection means 5 comprises a detection core 51 and a detection coil 52, arranged so that a magnetic field applied to the sample 20 by excitation means 4 induces eddy currents in the sample, and the magnetic field generated by these eddy currents are detected. The detection core 51 may, for example, be bracket-shaped, with the axial directions of both legs being oriented roughly perpendicular to the sample. The detection coil 52 is wound along the outer circumference of the detection core 51. This detection coil 52 may be wound over the entire circumference of the detection core 51, or only partially wound. If only partially wound, when wound on both legs of a bracket shape, one leg is wound clockwise and the other leg is wound counterclockwise, and the end of the winding of one leg is coupled to the beginning of the winding of the other leg to form a single continuous coil.

Next, the actions when performing inspection using a non-destructive inspection device 30 using a magnetic field according to the present invention shall be explained with reference to FIG. 1. Herebelow, a method and device for canceling the dominant component of the detection coil output by taking the sum (addition) of the detected coil output and a voltage signal of the same amplitude and opposite phase shall be explained. It can also be arranged to cancel the dominant component of the detection coil output by taking the difference (subtraction) between the detected coil output and a voltage signal of the same amplitude and same phase. In this case, during the phase adjustment between the detected output and the reference signal to be explained below, the phase of the detected coil output is set to the same phase as the reference signal, the amplitude of the reference signal is set to be equal to the amplitude of the detected coil output, and the difference between the detected coil output and the reference signal is taken. Herebelow, a method and device for canceling the dominant component of the detected coil output by taking the sum of the detected coil output and a reference signal of the same amplitude and opposite phase shall be described.

First, the switch S is set to the S1 side. As a result, the output A (reference signal) of the signal waveform generator 1 is supplied to only the amplifier circuit 9, and not to the potentiometer 6.

The frequency of the signal waveform generator 1 is determined. Output B and output A are set to the same frequency. The frequency is determined in consideration of the material of the sample and the location of inspection.

Of the outputs from the signal waveform generator 1, output B is current-amplified by the power amp 3 and sent to the excitation coil 42. The AC current flowing through the excitation coil generates an alternating excitation magnetic field. A large portion of the excitation magnetic field is concentrated at the excitation core 41, from the end surface of which it is directed toward the surface of the sample 20. The magnetic field in the excitation coil 41 is oriented in a single direction at any one moment. For example, if the excitation core 41 is bracket-shaped with the axial directions of both legs being oriented roughly perpendicular to the surface of the sample 20, then from the viewpoint of the sample 20, the magnetic field applied from the end surface of one leg and the magnetic field applied from the end surface of the other leg will be directed opposite each other, and the magnetic field inside the excitation core will be directed from the one leg to the other leg. Because the applied magnetic field is due to an AC current, the direction will alternate.

By applying a magnetic field to the sample 20 by means of the excitation means 4, eddy currents are induced in the sample 20, and these eddy currents generate a magnetic field. When the excitation core 41 is, for example, bracket-shaped with the axial directions of both legs oriented roughly perpendicular to the sample, eddy currents are induced in the sample 20 at two locations on the sample 20 centered at a position where both end surfaces of the bracket-shaped excitation core 41 oppose each other, these eddy currents being oriented in opposite directions. This is due to the fact that the orientations of the magnetic fields applied to the sample 20 from the end surfaces of the excitation core 41 are in opposite directions. The eddy currents induced at these two locations generate respectively opposing magnetic fields.

The magnetic field generated at two locations on the sample 20 is detected by detecting means 5 provided near the excitation means 4, and a voltage is induced in the detection coil. If the detecting means 5 comprises a bracket-shaped detection core 51 and a detection coil 52 wound in opposite directions around both legs, with the end of one winding being coupled to the beginning of the other winding, then the magnetic field generated at the two locations on the sample 20 will be oriented in opposite directions, so the magnetic field entering one leg of the detection core 51 will be directed toward the other leg (it will alternate due to the AC current), and a voltage proportional to the sum of the number of windings wound about each leg will be induced in the detection coil 52.

The output voltage of the detection coil 52 is suitably amplified in the amplifier circuit 8, and the output can be confirmed at the check terminal TP-2. On the other hand, of the outputs of the signal waveform generator 1, the output A (reference signal) is suitably amplified by the amplifier circuit 9, and the output can be confirmed at the check terminal TP-1. The outputs of the check terminal TP-1 and check terminal TP-2 are simultaneously displayed on an oscilloscope with the horizontal axis representing time and the vertical axis representing voltage, using the computer 11. During the display, a trigger function is used to fix the trace. The AD converter which is needed for computer measurement may be contained in the soundboard if the computer 11 is equipped with a soundboard, or may be provided externally. Additionally, it may be performed using measurement software comprising an AD converter installed on the computer 11. Furthermore, the display of the outputs of the check terminal TP-1 and check terminal TP-2 is not limited to computer measurement, and they may of course be displayed using an oscilloscope measuring device with the horizontal axis representing time and the vertical axis representing voltage.

The phase of the output B of the signal waveform generator 1 is adjusted by a phase shifter 2 so that the time waveform of the check terminal TP-2 becomes of opposite phase with respect to the check terminal TP-1 on the oscilloscope display on the computer 11. As a result, the detection coil output voltage and the output A (reference signal) of the signal waveform generator 1 are set to mutually opposite phase.

Next, the switch S is set to contact S2. As a result, the output A (reference signal) of the signal waveform generator 1 is supplied to both the amplifier circuit 9 and the potentiometer 6.

Of the output A (reference signal) of the signal waveform generator 1, the signal output supplied via the switch S2 through the potentiometer 5 to the computing circuit 7 is summed with (added to) the output voltage of the detection coil 52. After the computed results of the computing circuit 7 are amplified by the amplifier circuit 8, they are displayed on the oscilloscope of the computer 11 as the output of the check terminal TP-2. The oscilloscope display on the computer 11 shows both the output of check terminal TP-2 and the output of check terminal TP-1.

The amplitude of the reference signal inputted to the computing circuit from the output A (reference signal) of the signal waveform generator 1 through the contact S2 of the switch S is adjusted by continuously varying the resistance by turning the volume dial of the potentiometer 6. Since the output A (reference signal) of the signal waveform generator 1 and the output voltage of the detection coil 52 are already set to be of mutually opposite phase, the amplitude of the output A (reference signal) branched through the contact S2 of switch S can be tuned to set the wave height of the voltage waveform at check terminal TP-2 to roughly zero (such that the dominant phase components before tuning are cancelled, leaving a low-amplitude voltage of different phase), thereby matching the amplitude of the output A (reference signal) branched through the contact S2 of switch S to the amplitude of the detected coil output. The low-amplitude voltage signal of different phase remaining after canceling out the dominant phase component from the output of the detection coil 52 is the detection signal for the magnetic field due to the eddy currents induced inside the sample 20 that was masked by the detection signal of the magnetic field due to the strong eddy currents induced at the surface portion of the sample 20. This tuning process may further involve adjusting the resistance of the potentiometer until the check terminal TP-3 indicating the output of the detector circuit 10 being monitored by check terminal TP-3 is made as close to zero as possible, thereby almost certainly canceling the detection components of the magnetic field due to eddy currents at the sample surface. The detector circuit 10 should preferably be a synchronous detector circuit. In that case, the output of the detector circuit 10 gives the direction cosine of the voltage signal of the output of computing circuit 7 amplified by the amplifier circuit 8 with respect to the output A (reference signal) of the signal waveform generator 1, so by tuning the resistance of the potentiometer 6 such that the output of the detector circuit 10 is made as close to zero as possible, the small residual component left by the computing circuit 7 for the detected component of the magnetic field due to eddy currents at the sample surface portion may be almost certainly eliminated. In this way, the strong detection output of the sample surface portion due to the skin effect can be canceled by setting the output of the potentiometer 6, enabling detection of the output inside the sample which was masked by the detected output of the sample surface portion.

As a result, the output of the potentiometer 6 as the reference signal inputted to the computing circuit 7 from the output A (reference signal) of the signal waveform generator 1 through the contact S2 of the switch S is set to be a voltage signal of the same amplitude and opposite phase with respect to the output of the detection coil 52. As a result, the detection component of the magnetic field due to eddy currents induced at the sample surface portion, which is the dominant component, can be effectively canceled from the output voltage of the detection coil 52.

Example 1

Figure 2:
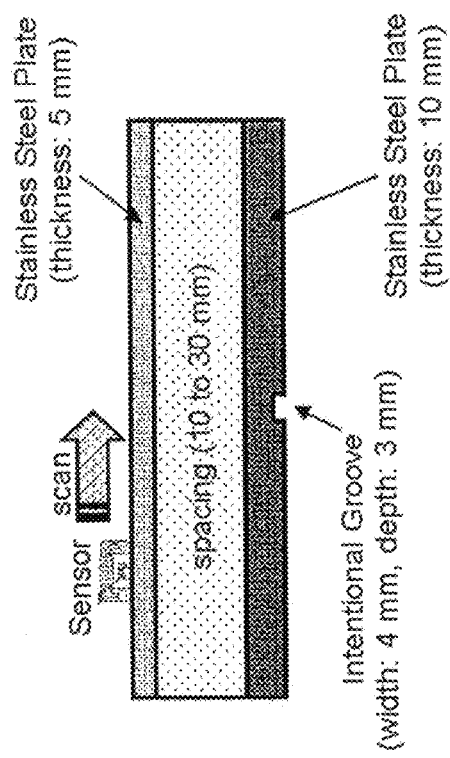
FIG. 2 is a schematic diagram showing an example of the present invention, for explaining an arrangement in a test for detecting an intentionally formed groove on the back surface of a lower steel plate from the outer surface of an upper steel plate of a stainless steel plate of dual structure.

FIG. 2 is a schematic diagram for explaining how a double stainless steel plate structure obtained by arranging two stainless steel plates with a gap in between was used to detect a groove intentionally formed on the back surface of the lower steel plate from the outside surface of the upper steel plate. The size of the steel plates, both upper and lower, was 600 mm in width and 400 mm in length, and the thickness was 5 mm for the upper steel plate and 10 mm for the lower steel plate. On the back surface of the lower steel plate, a groove of width 4 mm, depth 3 mm and length 400 mm was intentionally formed at the center of the steel plate (a position 300 mm from the end surface in the longitudinal direction). The gap between the steel plates was made variable from 10 mm to 30 mm in 5 mm increments using commercially available NR sponge rubber.

Figure 3:
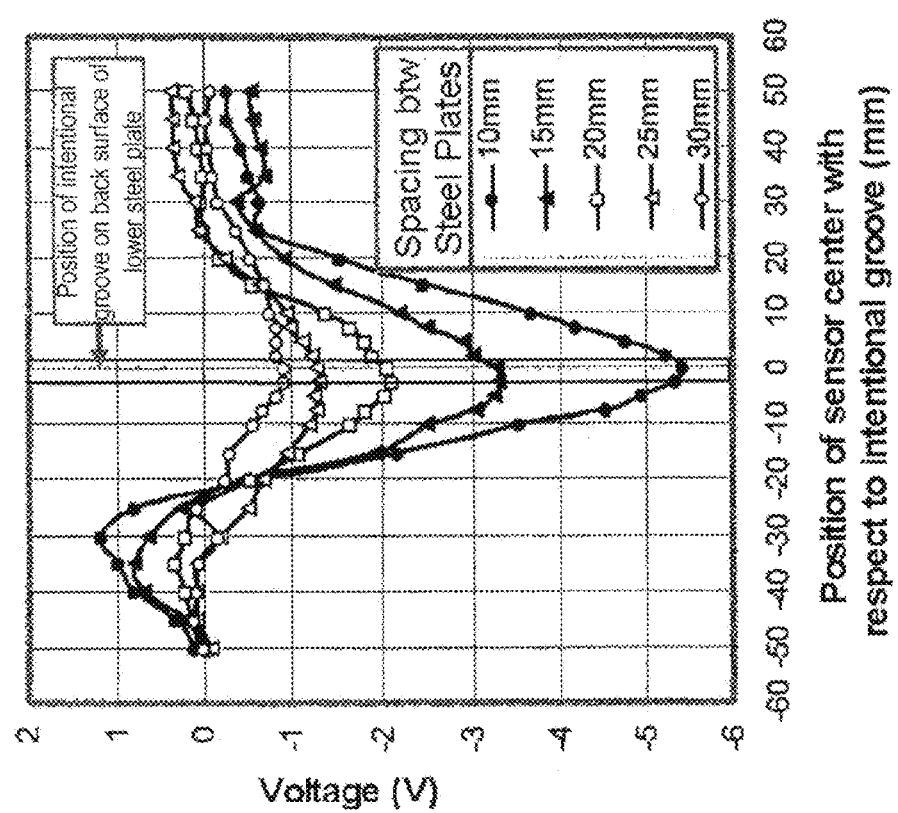
FIG. 3 is a diagram showing an example of detection of the intentionally formed groove in the back surface of the lower steel plate from the outer surface of the upper steel plate.

FIG. 3 shows the results of detection performed using the non-destructive inspection device of the present invention. The intentionally formed groove (width 4 mm, depth 3 mm) on the back surface of the lower steel plate (10 mm thick) was able to be detected from the outside surface of the upper steel plate (5 mm thick). Although more clearly detected when the gap between the upper steel plate and the lower steel plate was smaller, it was demonstrated to be detectable even with a gap of 30 mm. This test result shows that damage to the inner wall of the inner pipe of a double pipe can be detected from the outside surface of the outer pipe, which raises expectations for the possibility of pioneering new objects of inspection by non-destructive inspection.

Example 2

Figure 4:
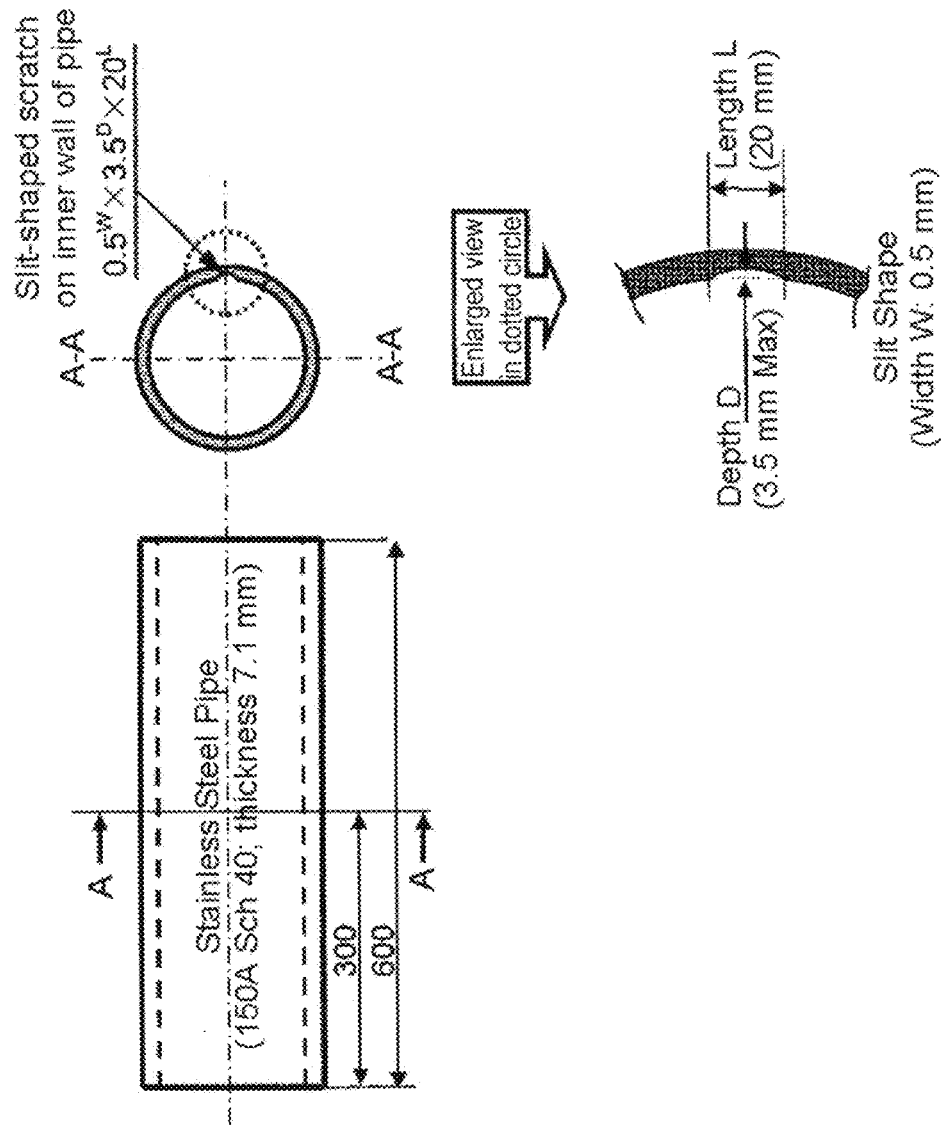
FIG. 4 is a diagram showing another example of the present invention, for schematically explaining a test piece used in a test for detection of microscopic flaws on the inner walls of a stainless steel pipe.

FIG. 4 is a diagram for schematically explaining a test piece used in a test for detecting minor scratches in the inner walls of a stainless steel pipe. The stainless steel pipe was a 150 A schedule pipe (Sch 40) of plate thickness 7.1 mm. Slit-shaped scratches of width 0.5 mm, depth 3.5 mm and length 20 mm were formed in the circumferential direction of the inner wall of the pipe by discharge processing, and detection tests were performed for these minor scratches by the non-destructive inspection devices of the present invention with some lift-off from the outer surface of the pipe.

Figure 5:
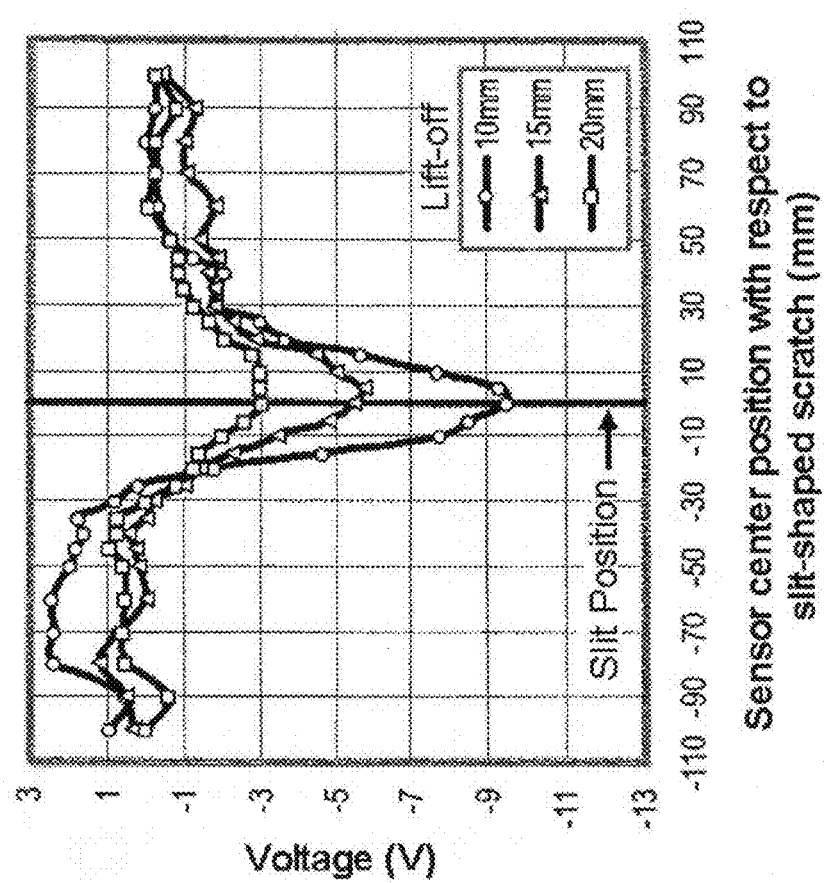
FIG. 5 is a diagram showing an example of detection of microscopic flaws on the inner walls of a stainless steel pipe.

The results of the tests for detecting minor scratches on the inner walls of the stainless steel pipe are shown in FIG. 5. Slit-shaped scratches (width 0.5 mm, depth 3.5 mm max, length 20 mm) in the inner walls of a stainless steel pipe of plate thickness 7.1 mm were able to be clearly detected from the outer surface of the pipe even with 20 mm of lift-off.

Example 3

Figure 6:
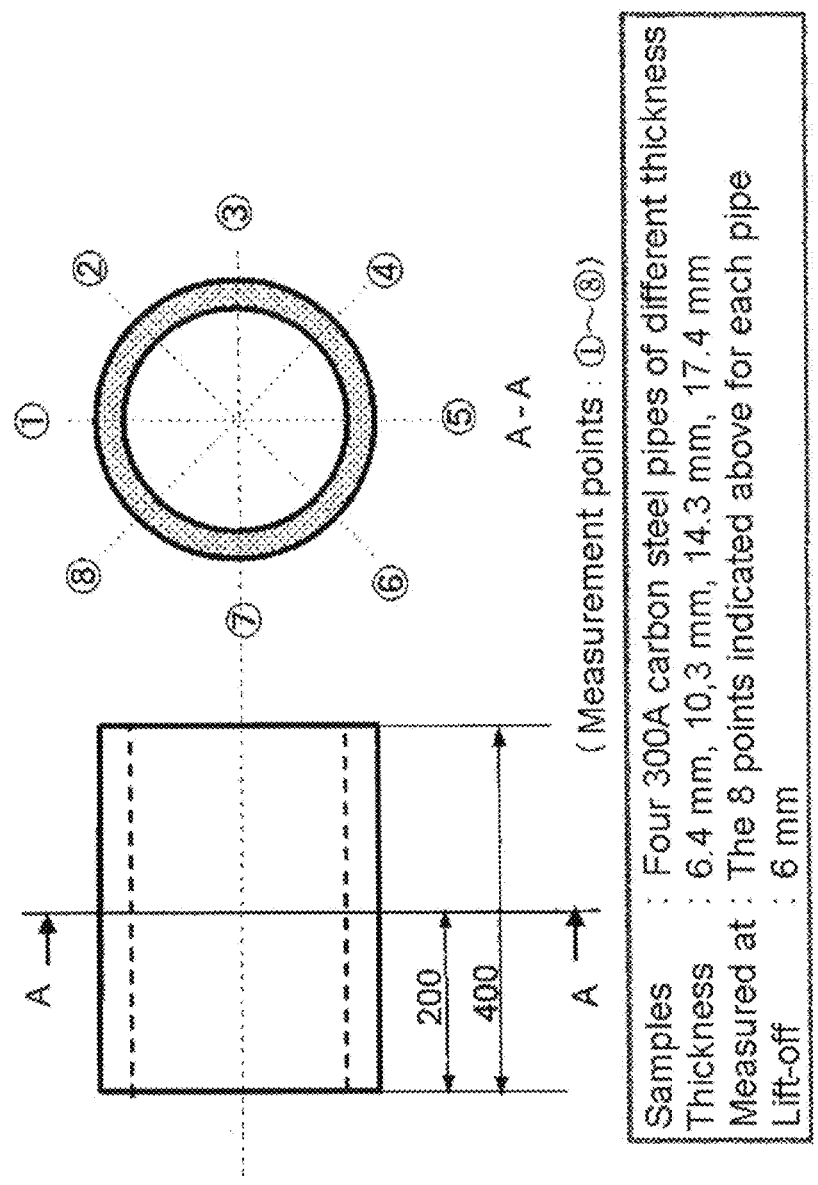
FIG. 6 is a schematic diagram showing an example of the present invention, for explaining the shape and parts to be measured of a test piece used in thickness measurement of a carbon steel pipe.

FIG. 6 is a diagram for explaining the shape of the test pieces used and the parts measured in the measurement of thickness of a carbon steel pipe. The test pieces were four 300 A carbon steel pipes of different thicknesses, the thicknesses being respectively 6.4 mm, 10.3 mm, 14.3 mm and 17.4 mm. Each pipe was a commercially available pipe purchased by designating the size, used without processing of any kind. The portions measured were eight equidistantly spaced points on the outer circumference at the middle (a position 200 mm from the pipe end surface) of each pipe, each point being measured with a lift-off of 6 mm from the pipe surface.

Figure 7:
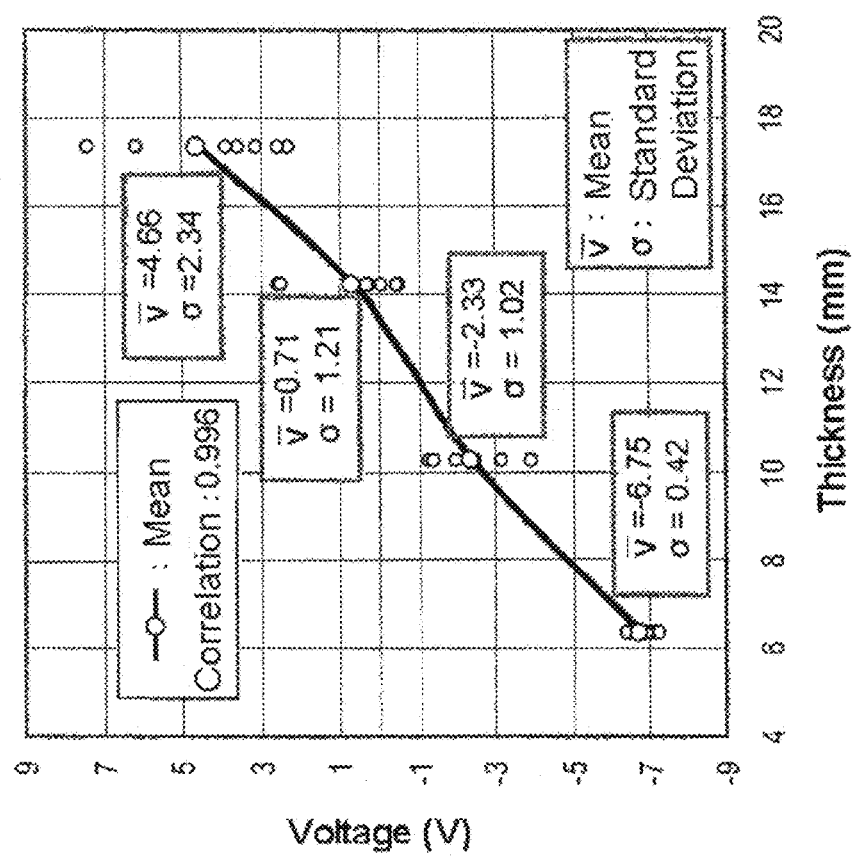
FIG. 7 is a diagram showing the results of thickness measurement of a carbon steel pipe.

FIG. 7 shows the results of measurement of thickness of a 300 A carbon steel pipe. The measurement values at the eight points are shown for the pipe of each thickness, and the mean and standard deviation were computed from the measurements for each thickness, the results being shown in the diagram. The units for the mean and standard deviation are voltages [V]. As the plate becomes thicker, the variation tends to become greater, but there is an extremely high correlation (correlation coefficient $r=0.996$) between pipe thickness and detected output. As a result, the detection of the thickness of thick carbon steel pipes, which was not conventionally possible, was made possible. A thickness reduction of 30% was able to be detected at a probability of at least 96%, and a thickness reduction of 40% was able to be detected at a probability of at least 99%.

Example 4

Figure 8:
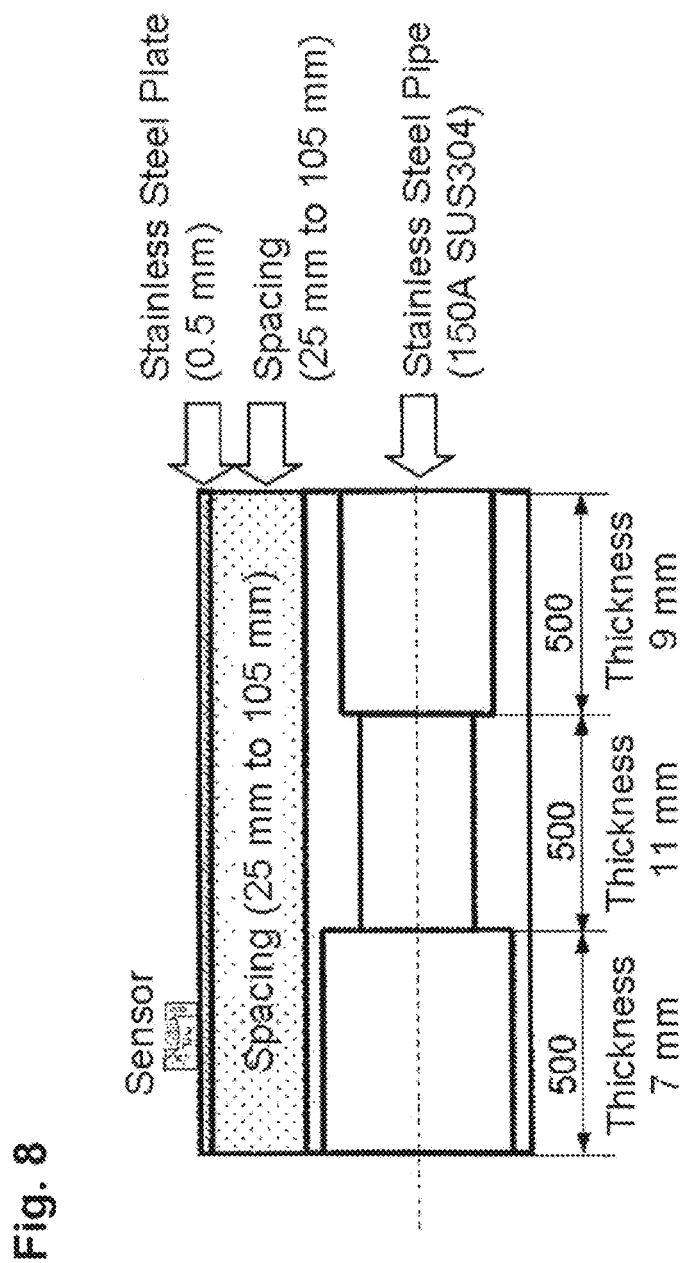
FIG. 8 is a diagram showing another example of the present invention, for schematically explaining an arrangement for performing thickness measurements of a stainless steel pipe placed directly under and across a gap from the surface of a stainless steel sheet.

FIG. 8 is a diagram for schematically explaining how the thickness of a stainless steel pipe placed directly below is measured across a gap from the surface of a stainless steel sheet. The pipe was a 150 A Sch 80 SUS304 pipe (thickness 11 mm, length 1.5 m), from both end surfaces a length of 500 mm was cut to produce test pieces of thickness 7 mm, 9 mm and 11 mm. The sheet on the top surface was an SUS304 steel plate of thickness 0.5 mm. The gap between the sheet and the pipe was variable between 25 mm and 105 mm in 20 mm increments using a commercially available NR sponge rubber. The sensor lift-off from the top surface sheet was 0.2 mm.

Figure 9:
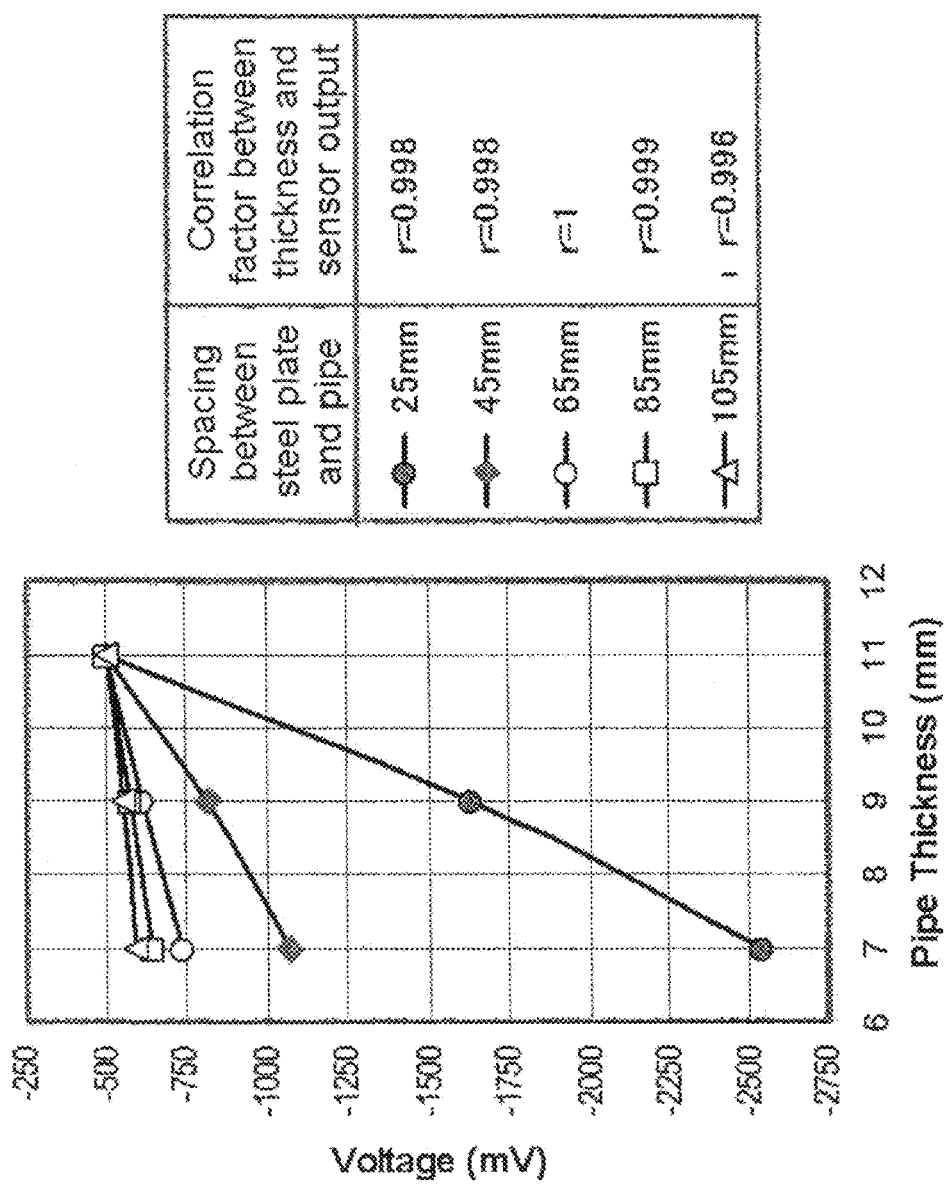
FIG. 9 is a diagram showing the results of pipe thickness measurement.

FIG. 9 shows the results of thickness measurement of the pipe. A very high correlation was observed between the detected output of the sensor and the thickness of the pipe. This high correlation was such that a correlation factor of at least $r=0.99$ was obtained between the pipe thickness and the detected output irrespective of the distance (25 mm to 105 mm) between the top sheet and the pipe being inspected, and a linear dependency was observed between the pipe thickness and the detected output. These test results show that the change in thickness of a steel pipe covered with a metallic external covering material and tens of millimeters of a condensation preventing material can be inspected with high precision from outside the condensation preventing material.

Example 5

Figure 10:
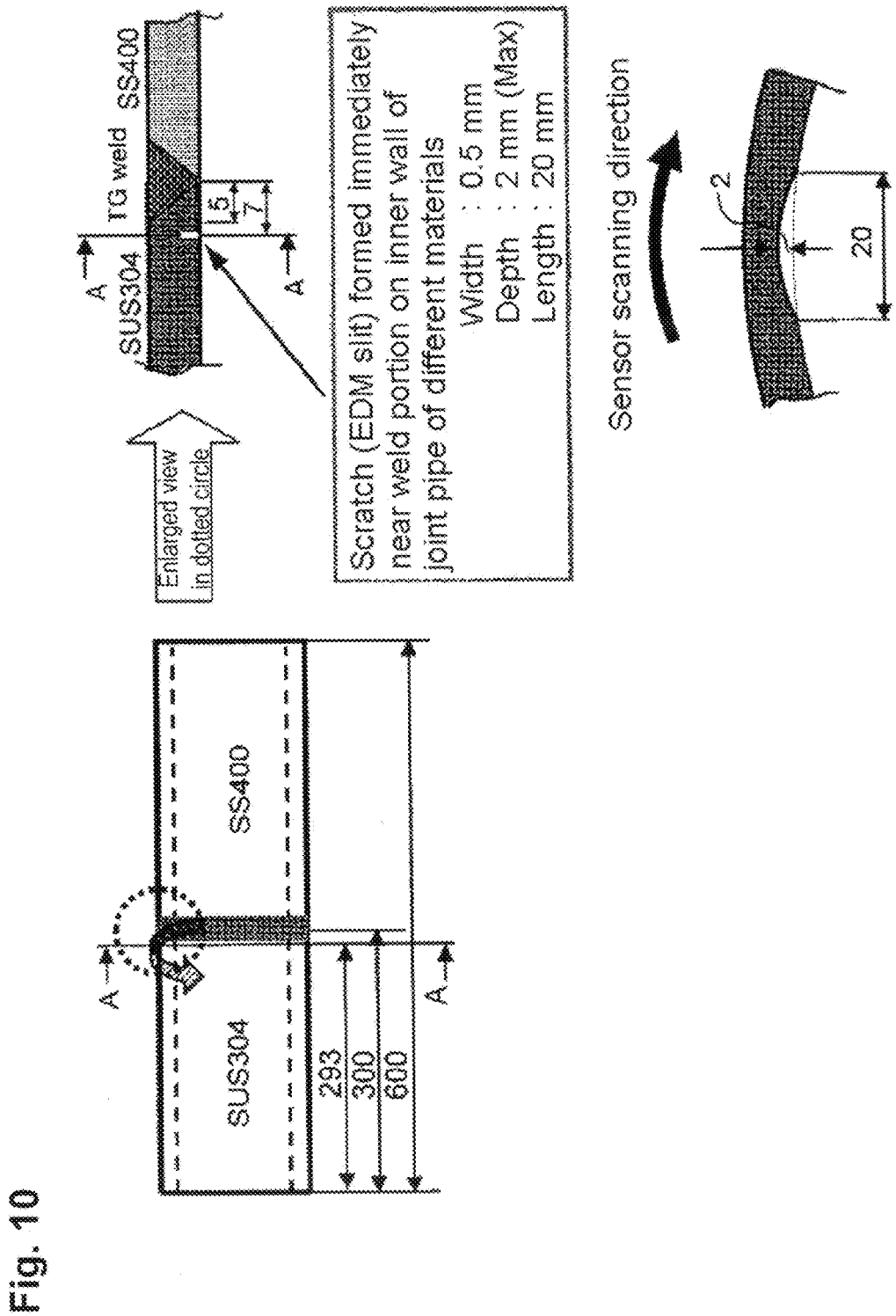
FIG. 10 is a schematic diagram showing an example of the present invention, for explaining an example of detection of microscopic flaws formed near a welding portion on the inner wall of a joint pipe of different materials such as stainless steel and carbon steel.

FIG. 10 is a diagram for explaining examples of detection of minor scratches formed near a weld portion on the inner walls of joint pipes of different materials such as stainless steel and carbon steel, for schematically explaining the test pieces and tests. The test pieces have slit-shaped scratches (width 0.5 mm, depth 2 mm max, length 20 mm) formed by discharge processing on the SUS-side HAZ portion (heat affected zone) on the inner wall of a joint pipe of different materials 150 A SUS304 and SS400. The measurements were scanned in the circumferential direction of the pipe over the external surface of the pipe directly above the slit scratches made inside the pipe.

Figure 11:
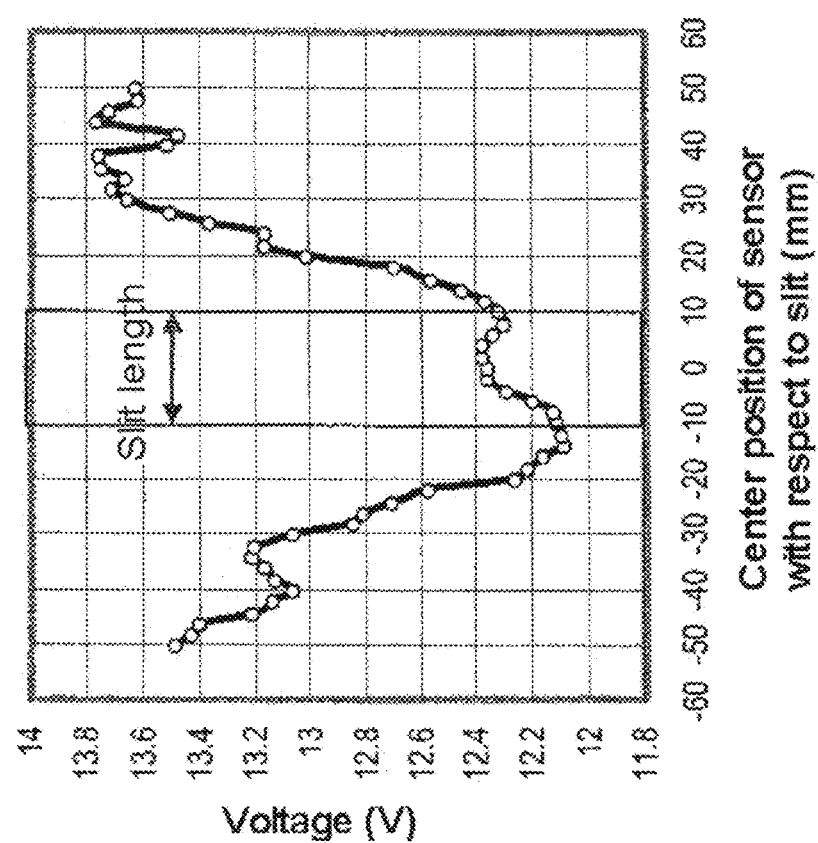
FIG. 11 is a diagram showing the results of detection of microscopic flaws formed near a welding portion on the inner wall of a joint pipe of different materials.

FIG. 11 shows the results of detection of minor scratches provided near the weld portion on the inner wall of a joint pipe of different materials. A clear change (downward bulge) was observed in the detected output of the sensor corresponding to the position of the minor scratch. This shows that minor scratches near a weld portion on the inner wall of a pipe can be detected from outside the pipe.

MODES FOR CARRYING OUT THE INVENTION 1 signal waveform generator
2 phase shifter
3 power amp
4 excitation means
5 detection means
6 potentiometer
7 computing circuit
8 amplifier circuit
9 amplifier circuit
10 detector circuit
11 computer
20 sample

What is claimed is:

1. A non-destructive inspection device using an alternating magnetic field, comprising:
 a signal waveform generator;
 an excitation coil and an excitation core configured to apply the alternating magnetic field to a sample;
 a detection coil and a detection core nearby positioned and surrounded by the excitation coil and the excitation core configured to sense a magnetic field due to eddy currents generated from the sample;
 a circuit comprising a circuit configured to generate a sinusoidal signal of approximately equal amplitude and opposite phase with respect to a detected signal of the detection coil and the detection core, and configured to output a sum of an output of the opposite-phase sinusoidal signal generating circuit and the detected signal of the detection coil and the detection core; and
 detecting circuitry configured to detect a remainder signal which is the sum of the output of the opposite-phase sinusoidal signal generating circuit and the detected signal,
 wherein the excitation core is bracket-shaped, the excitation coil is wound over the entire circumference of the excitation core, and the axial directions of both legs of the excitation core are oriented roughly perpendicular to the sample,
 wherein the detection core is bracket-shaped, the detection coil is wound only over short side parts of the detection core, and the axial directions of both legs of detection core are oriented roughly perpendicular to the sample, and
 wherein a detected output of a surface portion of the sample due to a skin effect is canceled to detect the output inside the sample which was masked by the detected output of the surface portion of the sample.

2. The non-destructive inspection device of claim 1, wherein the sample is a material having electrical conductivity.

3. The non-destructive inspection device of claim 1, wherein the detecting circuitry is a synchronous detection circuit.

4. A non-destructive inspection device using an alternating magnetic field, comprising:
 a signal waveform generator;
 an excitation coil and an excitation core configured to apply the alternating magnetic field to a sample;
 a detection coil and a detection core nearby positioned and surrounded by the excitation coil and the excitation core configured to sense a magnetic field due to eddy currents generated from the sample;
 a circuit comprising a circuit configured to generate a sinusoidal signal of approximately equal amplitude and in-phase with respect to a detected signal of the detection coil and the detection core, and configured to output a difference between an output of the in-phase sinusoidal signal generating circuit and the detected signal of the detection coil and the detection core; and
 detecting circuitry configured to detect a remainder signal which is the difference between the output of the in-phase sinusoidal signal generating circuit and the detected signal,
 wherein the excitation core is bracket-shaped, the excitation coil is wound over the entire circumference of the excitation core, and the axial directions of both legs of the excitation core are oriented roughly perpendicular to the sample,
 wherein the detection core is bracket-shaped, the detection coil is wound only over short side parts of the detection core, and the axial directions of both legs of detection core are oriented roughly perpendicular to the sample, and
 wherein a detected output of a surface portion of the sample due to a skin effect is canceled to detect the output inside the sample which was masked by the detected output of the surface portion of the sample.

5. The non-destructive inspection device of claim 4, wherein the sample is a material having electrical conductivity.

6. The non-destructive inspection device of claim 4, wherein the detecting circuitry is a synchronous detection circuit.

7. A non-destructive inspection method for a sample, comprising:
 outputting a signal using a signal waveform generator;
 applying an alternating magnetic field to the sample using an excitation coil and an excitation core;
 detecting a magnetic field due to eddy currents generated from the sample using a detection coil and a detection core nearby positioned and surrounded by the excitation coil and the excitation core;
 outputting a sum of a detected signal of the detection coil and the detection core and a sinusoidal signal of approximately equal amplitude and opposite phase with respect to the detected signal of the detection coil and the detection core; and detecting a remainder signal which is the sum of the detected signal and the sinusoidal signal, wherein the excitation core is bracket-shaped, the excitation coil is wound over the entire circumference of the excitation core, and the axial directions of both legs of the excitation core are oriented roughly perpendicular to the sample, wherein the detection core is bracket-shaped, the detection coil is wound only over short side parts of the detection core, and the axial directions of both legs of detection core are oriented roughly perpendicular to the sample, and wherein a detected output of a surface portion of the sample due to a skin effect is canceled to detect the output inside the sample which was masked by the detected output of the surface portion of the sample.

8. A non-destructive inspection method for a sample, comprising:

outputting a signal using a signal waveform generator;

applying an alternating magnetic field to the sample using an excitation coil and an excitation core;

detecting a magnetic field due to eddy currents generated from the sample using a detection coil and a detection core nearby positioned and surrounded by the excitation coil and the excitation core;

outputting a difference between a detected signal of the detection coil and the detection core and a sinusoidal signal of approximately equal amplitude and in-phase with respect to the detected signal of the detection coil and the detection core; and detecting a remainder signal which is the difference between the detected signal and the sinusoidal signal, wherein the excitation core is bracket-shaped, the excitation coil is wound over the entire circumference of the excitation core, and the axial directions of both legs of the excitation core are oriented roughly perpendicular to the sample, wherein the detection core is bracket-shaped, the detection coil is wound only over short side parts of the detection core, and the axial directions of both legs of detection core are oriented roughly perpendicular to the sample, and wherein a detected output of a surface portion of the sample due to a skin effect is canceled to detect the output inside the sample which was masked by the detected output of the surface portion of the sample.

* * * * *